United States Patent [19]

Dunn et al.

[11] Patent Number: 5,665,757
[45] Date of Patent: Sep. 9, 1997

[54] METHOD FOR TREATING ANXIETY

[75] Inventors: Robert W. Dunn, P.O. Box 894, Old Lyme, Conn. 06371; Suzanne La Marca, Cliffwood Beach, N.J.

[73] Assignee: Robert W. Dunn, Warren, N.J.

[21] Appl. No.: 274,596

[22] Filed: Jul. 13, 1994

[51] Int. Cl.$^6$ .................................................. A61K 31/415
[52] U.S. Cl. ........................ 514/403; 514/405; 514/551; 514/564
[58] Field of Search .................... 514/405, 551, 514/403, 564

[56] References Cited

U.S. PATENT DOCUMENTS

| | | | |
|---|---|---|---|
| 5,216,025 | 6/1993 | Gross et al. | 514/565 |
| 5,246,970 | 9/1993 | Williamson et al. | 514/632 |
| 5,246,971 | 9/1993 | Williamson et al. | 514/634 |
| 5,286,739 | 2/1994 | Killbourn et al. | 514/400 |

OTHER PUBLICATIONS

Haefely, *Eur. Neuropsychopharmacol.*, vol. 1, 89–95 (1991).
Perregaard et al., *Curr. Opin. Ther. Pat.*, vol. 3, 101–128 (1993).
Rees et al., *Br. J. Pharmacol.*, vol. 101, pp. 746–752 (1990).
Moore et al., Br. J. Pharmacol, vol. 110, pp. 219–224 (1993).
Moore et al., *Br. J. Pharmacol*, vol. 108, pp. 296–297 (1993).
Lowenstein et al., *Cell*, vol. 70, pp. 705–707 (1992).
Meller et al., *Pain*, vol. 52, pp. 127–136 (1993).
Feldman et al., *C&EN*, pp. 26–38 (Dec. 1993).
Feldman et al. *Chemtracts—Organic Chemistry*, 5 pp. 217–221 (1992).
Life Sciences, vol. 51, No. 25, Quock et al., "Possible Involvement of Nitric Oxide in Chlordiazepoxide–Induced Anxiolysis in Mice", 1992, pp. PL–255–260.
Pharmacology Biochemistry and Behavior, vol. 48, No. 3, Caton et al., "Involvement of Nitric Oxide in Nitrous Oxide Anxiolysis in Elevated Plus–Maze", 1994, pp. 689–692.
Perregaard et al., "Recent Developments in Anxiolytics", Jan. 1993, Carr. Opin. Ther. Pat., vol. 3, pp. 111–112.
Rees et al., "Characterization of Three Inhibitors of Endothelial Nitric Oxide Synthase in Vitro and in Vivo", 1990, Br. J. Pharmacol., 101 pp. 746–751.
Moore et al., "Characterization of the Novel Nitric Oxide Synthase Inhibitor 7–nitro Indazole and Related Indazoles: Antinoceptive and Cardiovascular Effects", Br. J. Pharmacol. vol. 110 pp. 219–224.

*Primary Examiner*—Gary Geist
*Assistant Examiner*—Rosalynd Williams
*Attorney, Agent, or Firm*—Watov & Kipnes, P.C.

[57] ABSTRACT

A method of treating anxiety in a warm blooded animal by administering an anti-anxiety effective amount of a nitric oxide synthase inhibitor, and compositions containing the same.

6 Claims, No Drawings

METHOD FOR TREATING ANXIETY

The present invention is directed to a method of treating anxiety in a warm-blooded animal by administering to said warm-blooded animal an anti-anxiety effective amount of a nitric oxide synthase inhibitor.

BACKGROUND OF THE INVENTION

Anxiety is a fundamental emotion and a normal response in some warm-blooded animals, including humans, which is characterized by an apprehensive uneasiness of mind usually associated with an impending or anticipated experience that may be problematic. When such apprehension becomes disproportionate and overwhelming, it is termed an anxiety neurosis which can be characterized by helplessness, tension, uneasiness, faintness, or even panic. This anxiety state can also be accompanied by physiological signs such as rapid heart rate, rapid breathing, sweating, dry mouth and nausea. The mechanism by which anxiety is induced in the Central Nervous System (CNS) is complex. A detailed discussion of the process is disclosed in, for example, Haefely W., "Psychopharmacology of Anxiety", *Eur. Neuropsychopharmacol.*, Vol. 1, pp. 89–95 (1991).

The ascending serotonergic raphe system and noradrenergic locus coeruleus pathways as well as the GABAergic system are involved in the genesis of the anxiety state. The cell bodies of origin of the serotonergic and noradrenergic systems are located in the brain region designated anatomically as the reticular formation while GABAergic neurons are located throughout the brain.

In general, both serotonin and noradrenergic neuronal transmission are increased during anxiety states. The GABAergic system, and specifically the neurotransmitter GABA, which is the major inhibitory transmitter in the CNS, acts as an agonist at the $GABA_A$, receptor complex to mediate inhibition through hyperpolarization due to an influx of $Cl^-$ at the ionophore. This hyperpolarization is achieved by allosteric modulation by an endogenous ligand substance for another site on this complex, the benzodiazepine receptor. The $GABA_A$-benzodiazepine receptor complex may become dysregulated in anxiety disorders and reduce the inhibitory regulation of the GABAergic system. Likewise, the glutamatergic system and its neurotransmitter glutamate, mediate excitatory activity in the CNS. Glutamate receptors, especially N-methyl-D-aspartate (NMDA) receptors, are located throughout the CNS and are also colocalized with $GABA_A$, receptors on the same neurons. This excitatory system may also become dysregulated in anxiety states.

Efforts at mediating anxiety have focused on modulating these neurotransmitter systems. A detailed discussion of anti-anxiety or anxiolytic agents used for the treatment of anxiety is disclosed in, for example, Jens Perregaard et al., "Recent Developments in Anxiolytics", *Curr. Opin. Ther. Pat.*, Vol. 3, pp. 101–128 (1993). For example, serotonergic agents ($5-HT_{1A}$ agonists, $5-HT_2$ antagonists and $5-HT_3$ antagonists), benzodiazepines and excitatory amino acid antagonists have demonstrated varying degrees of anxiolytic potential. In the glutamate based neurotransmitter system, excess glutamate activity may contribute to the induction of anxiety. Under these circumstances, glutamate binds to the N-methyl-D-aspartate (NMDA) receptor which then activates or opens the $Ca^{2+}$ ionophore such that $Ca^{2+}$ enters the neuron and activates calmodulin. This substance activates nitric oxide synthase which, in turn, is responsible for converting L-arginine into citrulline and nitric oxide. Nitric oxide is believed to activate guanylate cyclase to produce the second messenger cyclic guanosine monophosphate (cGMP) which may be directly involved in triggering the anxiety process.

There are at least three distinct forms of nitric oxide synthase (NOS) found in the body. The first type is neuronal NOS found principally in the CNS and in non-adrenergic, non-cholinergic (NANC) neurons in the gut. Endothelial NOS and inducible NOS (found in macrophages) are the second and third types. Endothelial NOS, found in the endothelial tissues, affects blood circulation by producing nitric oxide which acts as a vasodilator. Accordingly, endothelial NOS has been implicated in such conditions as hypertension, endotoxin shock (e.g. septic shock) and thrombosis.

Inducible NOS triggers the production of nitric oxide when the body is exposed to an endotoxin, and has been associated with such chronic ailments as ulcerative colitis and arthritis.

The production of nitric oxide can be inhibited by a class of compounds known as NOS inhibitors. For example, Interleukin-1 and lipopolysaccharides are known to inhibit the activity of macrophage NOS such as disclosed in Joseph R. Williamson et al., U.S. Pat. Nos. 5,245,970 and 5,246,971. Analogues of L-arginine including $N^G$-monomethyl-L-arginine (L-NMMA), N-iminoethyl-L-ornithine (L-NIO) and $N^G$-nitro-L-arginine methyl ester (L-NAME) have been shown to inhibit endothelial NOS. D. D. Rees et al., *Br. J. Pharmacol.*, Vol. 101, pp. 746–752 (1990). Analogues of indazole including 7-nitro-indazole have been shown to inhibit neuronal and endothelial NOS. P. K. Moore et al., *Br. J. Pharmacol.*, Vol. 110, pp. 219–224 (1993).

The present invention is premised on the discovery that compounds which effectively inhibit nitric oxide synthase, especially neuronal NOS, when administered in effective doses, can be employed as potent anti-anxiety agents.

SUMMARY OF THE INVENTION

The present invention provides a method of treating anxiety in a warm blooded animal comprising administering to said warm blooded animal an anti-anxiety effective amount of a nitric oxide synthase inhibitor. In a preferred form of the invention, the nitric oxide synthase inhibitor is one which inhibits at least neuronal nitric oxide synthase in the conversion of L-arginine to citrulline and nitric oxide. In a preferred form of the invention, the nitric oxide synthase inhibitor substantially inhibits the activity of neuronal nitric oxide synthase and minimally inhibits the activity of endothelial and/or inducible nitric oxide synthases. The administration of a nitric oxide synthase inhibitor in accordance with the present invention minimizes or eliminates the production of nitric oxide and thus the production of cyclic GMP. As a result, the anxiety state is attenuated.

DETAILED DESCRIPTION OF THE INVENTION

The present invention is directed to a method of treating anxiety through the administration of a nitric oxide synthase inhibitor. The term "treating" as utilized herein is intended to mean both prophylactic and curative applications. The compounds of the invention can be administered after the onset of the anxiety state, at the first appearance of symptoms indicating potential anxiety, and in those situations where anxiety is likely to occur, such as during preparation for surgery.

Specific examples of the nitric oxide synthase inhibitors for use in the present invention include L-$N^G$-nitro-arginine methyl ester (L-NAME), L-$N^G$-nitro-arginine (L-NOARG) and 7-nitro-indazole (7-NI). The nitric oxide synthase inhibitors of the present invention may be administered to a warm-blooded animal in amounts of at least 3 mg/kg of body weight of said animal, preferably from about 3 to 54.8 mg/kg of body weight.

The nitric oxide synthase inhibitors of the present invention are typically combined with a pharmaceutically acceptable carrier which is selected depending on the water-solubility of the specific inhibitor. Examples of suitable carriers include isotonic saline, distilled water, dilute hydrochloric acid, bicarbonates, dimethyl sulfoxide, mixtures of alcohols, such as ethanol and propylene glycol, and saline, and the like. For example, effective carriers include a mixture of 10% by volume of ethanol, 40% by volume of propylene glycol, and 50% by volume of saline as well as a mixture of 10% by volume (ethanol and emulphor; 2:1 ), 60% by volume propylene glycol and 30% by volume of saline.

Compositions for parenteral administration contain from about 0.1% to about 50% by weight of the nitric oxide synthase inhibitors of the subject invention. The amount present will depend on the potency of the active ingredient and its solubility in the pharmaceutical vehicle. In general, the compositions contain sufficient active ingredient so that the practitioner may titrate the dosage if desired and still be able to administer the maximum dosage in a parenteral container without giving the patient an unduly large amount of fluid. The nitric oxide synthase inhibitors may be combined with the carrier at room temperature, particularly when they are highly soluble in the carrier. For nitric oxide synthase inhibitors of lower solubility, it may be desirable to heat the carrier to temperatures below its boiling point to effect solution.

The composition containing the nitric oxide synthase inhibitor is administered parentally, preferably by intravenous injection. The composition of the present invention upon administration to a warm blooded animal, effectively prevents and alleviates anxiety.

The following examples illustrate preferred embodiments of the invention and are not intended to limit the scope of the invention as encompassed by the claims forming part of the application.

EXAMPLE 1

Naive male Sprague-Dawley rats (Hilltop Labs, Penn.) weighing 185–220 grams were individually housed in a vivarium for one week prior to testing with regularly available supplies of food and water. Rats (groups of 7 or 8) were water deprived for 48 hours prior to testing. The modified Vogel-lick shock conflict test was conducted in operant conditioning chambers consisting of a plexiglas cubicle (25×25×25 cm) with a stainless steel grid floor and an aluminum front panel equipped with an optical licometer (Coulbourn Instruments). J. R. Vogel et al., *Psychopharmacologia* (Berl.) Vol. 21, pp. 1–7 (1971).

Each rat was allowed to acclimate to the laboratory environment for at least 30 minutes. The test animals were then injected intravenously with one ml/kg of a composition containing $N^G$-nitro-L-arginine methyl ester (L-NAME) in saline in the dosage amounts shown in Table 1. The injection was made into the lateral vein of the tail. Thirty minutes later, each rat was placed in the lick-shock chamber and testing commenced. Test sessions were 5 minutes in length during which an electric shock (2.0 mA; 2.0 seconds) was administered on every 21st lick to minimize licking behavior in thirsty rats. The administration of shock caused a conflict or "fear" in control animals such that they would repress the desire to lick even though they were thirsty. Conflict responses, therefore, were the number of licks during the 5-minute test session. Agents which effectively disinhibit the conflict response show anxiolytic effects in the clinical setting.

The mean and standard error of the mean (SEM) for conflict responses was determined for each dose group and controls. The effect of the treatment is calculated as the percent change in conflict responses according to the following formula and is summarized in Table 1:

$$\frac{\text{Mean responses of inhibitor} - \text{mean responses of vehicle}}{\text{Mean responses of vehicle}} = \% \text{ change}$$

TABLE 1

| Dose (mg/kg, iv) | Conflict Responses (mean ± SEM) | % Change |
|---|---|---|
| 0 | 64.38 ± 9.84 | — |
| 30.0 | 118.25 ± 50.41 | +84 |
| 54.8 | 240.88 ± 64.98 | +274 |
| 100.0 | 158.38 ± 31.32 | +146 |

As shown in Table 1, administration of 30.0 mg/kg of body weight of the nitric oxide synthase inhibitor resulted in a significant increase in conflict responding (and therefore percent change) of the test animals, indicative of an anti-anxiety effect. As the dose was increased to 54.8 and 100.0 mg/kg of body weight, the percentage change in conflict responding increased to 274% and 146%, respectively, indicative of an anti-anxiety effect.

EXAMPLE 2

The test described in Example 1 was repeated except that the nitric oxide synthase inhibitor was L-$N^G$-nitro-arginine in the dosage amounts set forth in Table 2. The results are shown in Table 2.

TABLE 2

| Dose (mg/kg, iv) | Conflict Responses (mean ± SEM) | % Change |
|---|---|---|
| 0 | 74.80 ± 11.73 | — |
| 3.0 | 193.40 ± 63.91 | +159 |
| 10.0 | 186.80 ± 62.13 | +150 |
| 30.0 | 292.89 ± 81.30 | +292 |

As shown in Table 2, the administration of the composition of the present invention results in a significant increase in conflict responding (and therefore percent change) of the test animals, indicative of an anti-anxiety effect.

EXAMPLE 3

The test described in Example 3 was repeated except that the nitric oxide synthase inhibitor was 7-nitro-indazole in the dosage amounts set forth in Table 3. The results are set forth in Table 3.

TABLE 3

| Dose (mg/kg, iv) | Conflict Responses (mean ± SEM) | % Change |
| --- | --- | --- |
| 0 | 68.63 ± 9.70 | — |
| 3.0 | 142.00 ± 48.95 | +107 |
| 10.0 | 132.50 ± 28.93 | +93 |
| 17.3 | 410.00 ± 76.93 | +497 |

As shown in Table 3, the administration of the composition of the present invention results in a significant increase in conflict responding (and therefore percent change) of the test animals, indicative of an anti-anxiety effect.

EXAMPLE 4

The procedure described in Example 1 was repeated except that $N^G$-nitro-D-arginine methyl ester (D-NAME), a stereoisomer of L-NAME which is devoid of NOS inhibiting activity, was employed in the dosage amount set forth in Table 4. The results are shown in Table 4.

TABLE 4

| Dose (mg/kg, iv) | Conflict Responses (mean ± SEM) | % Change |
| --- | --- | --- |
| 0 | 58.38 ± 10.06 | — |
| 100.0 | 58.14 ± 24.07 | 0 |

As shown in Table 4, the administration of D-NAME was ineffective on conflict responding and therefore did not provide an anti-anxiety effect for the test animals.

EXAMPLE 5

In accordance with the procedure described in Example 1, L-Arginine, an amino acid substrate for nitric oxide synthase, was compared against the control and shown to produce a non-significant decrease in the number of conflict responses, and therefore had no effect on anxiety. As shown previously, the administration of L-NAME at 100 mg/kg results in a significant increase in conflict responses (and therefore percent change) of the test animals, indicative of an anti-anxiety effect. However, when L-NAME was administered immediately after L-arginine, the effect of L-NAME was essentially blocked. The results are shown in Table 5.

TABLE 5

| Compound | Dose (mg/kg, iv) | Conflict Responses (mean ± SEM) | % Change |
| --- | --- | --- | --- |
| Vehicle | 0 | 58.38 ± 10.06 | — |
| L-Arginine | 50.0 | 46.25 ± 6.77 | −21 |
| L-NAME | 100.0 | 119.17 ± 18.94 | +104 |
| L-Arginine + L-NAME | 50.0 + 100.0 | 46.25 ± 6.77 | −21 |

These results demonstrate the anti-anxiety effect of the nitric oxide synthase inhibitor (L-NAME) of the present invention is blocked by the effective competition for nitric oxide synthase (NOS) by the substrate therefor, L-arginine, showing that the anti-anxiety effect of L-NAME is due directly to inhibition of the enzyme nitric oxide synthase.

What is claimed:

1. A method of treating anxiety in a warm blooded animal comprising administering to said warm blooded animal an anti-anxiety effective amount of a nitric oxide synthase inhibitor.

2. A method in accordance with claim 1, wherein said nitric oxide synthase inhibitor inhibits the activity of at least neuronal nitric oxide synthase.

3. A method in accordance with claim 2, wherein said nitric oxide synthase inhibitor substantially inhibits the activity of neuronal nitric oxide synthase and minimally inhibits the activity of at least one of endothelial nitric oxide synthase and inducible nitric oxide synthase.

4. A method in accordance with claim 1, wherein the anti-anxiety effective amount of the nitric oxide synthase inhibitor is at least 3.0 mg/kg of body weight of said animal.

5. A method in accordance with claim 4, wherein the anti-anxiety effective amount of the nitric oxide synthase inhibitor is from about 3.0 to 100.0 mg/kg of body weight of said animal.

6. A method in accordance with claim 1, wherein the nitric oxide synthase inhibitor is selected from the group consisting of L-$N^G$-nitro-arginine methyl ester, L-$N^G$-nitro-arginine and 7-nitro-indazole.

* * * * *